United States Patent

Licari et al.

[11] B 3,983,270
[45] Sept. 28, 1976

[54] COMPOSITION FOR BOUNDARY LUBRICANT AND METHOD

[75] Inventors: James J. Licari, Whittier; Robert Willing, Anaheim, both of Calif.

[73] Assignee: Rockwell International Corporation, El Segundo, Calif.

[22] Filed: Oct. 26, 1973

[21] Appl. No.: 409,848

[44] Published under the second Trial Voluntary Protest Program on January 27, 1976 as document No. B 409,848.

[52] U.S. Cl. ............................ 427/372; 260/438.5 C
[51] Int. Cl.² .......................................... C23C 1/10
[58] Field of Search ............... 252/35; 117/127; 260/438.5 C, 414; 427/372

[56] References Cited
OTHER PUBLICATIONS

*Metal Organic Compounds,* "Chromium Complexes" Hauserman; 1959 ACS, pp. 339–356.

*Primary Examiner*—Mayer Weinblatt
*Assistant Examiner*—Edith R. Buffalow
*Attorney, Agent, or Firm*—H. Fredrick Hamann; G. Donald Weber, Jr.; Robert Ochis

[57] ABSTRACT

A composition for forming a boundary lubricant for metal and ceramic wear surfaces consisting of transition element complexes, including those of the higher molecular weight carboxylic acids such as the long chain fatty acids ($C_xH_{2x+1}$ COOH; $x = 8, 9, 10, \ldots$ 29). The transition elements used here are metals such as Cr, Mn, Fe, Co, Ni or Al that can form coordination complexes. Exemplary metal complexes are chromium stearate and chromium behenate.

An exemplary complex may be prepared by (1) reducing chromium trioxide by a reducing alcohol in a low molecular weight organic acid to produce chromium acetate; then 2 hydrating and olating the chromium acetate. A solution containing a maximum concentration of about 11 weight percent of the transition metal complex in a solvent such as trichloroethylene is applied as a thin layer onto a wear surface, then the layer is heated for 1–4 hours at a temperature at or above 70°C and, within the approximate range 70°–160°C. The transition metal complex chemically adheres to the wear surface, and is cross-linked by the heat treatment, to form an anchored, polymerized array of molecules that provides a hydrophobic, durable, boundary lubricant having a low coefficient of friction.

The transition metal complex solution may be applied to non-porous wear surfaces or, alternatively, may be impregnated into chrome oxide coatings or other porous refractory coatings on wear surfaces to form a porosity-filling boundary lubricant thereon. The lubricant decreases the clearance required between porous bearing surfaces, decreases the formation of corrosion cells, and lowers the coefficient of friction. The preferred amount of fatty acid or organic polyacid that can be stably incorporated into a complex chromium soap for use as a porosity-filling lubricant, that is, the optimum fatty acid mol/chromium gm-atom ratio, is approximately 1–1.2/1.

9 Claims, 5 Drawing Figures

COMPOSITION FOR BOUNDARY LUBRICANT AND METHOD

The invention herein described was made in the course of, or under a contract or subcontract thereunder, with the Navy.

BACKGROUND OF THE INVENTION

1. Field of the Invention

This invention relates to boundary lubricants for metal and ceramic wear surfaces such as those used in close tolerance hydrodynamic bearings, cams, or sliding-on-wear surfaces.

2. Description of the Prior Art

Metal or ceramic wear surfaces such as iron, steel, chromium, nickel, silicon, quartz and sapphire, for applications such as gyroscope spin bearing parts, rolling-and-sliding element bearings, machine parts, and cams impose stringent requirements on boundary lubricants used to reduce wear and friction between the surfaces.

Present methods of lubrication do not combine durable wear and friction resistance characteristics. For example, oil-type lubricants, which are not true boundary lubricants, move relative to the wear surfaces, decompose under the resulting frictional contact, and provide a vehicle for the agglomeration of metal wear particles.

Classic boundary lubricants include stearates, such as heavy metal or sodium stearate, and simple fatty acids, such as stearic acid ($CH_3(CH_2)_{16}COOH$). (The use of fatty acids and metal salts of fatty acids, such as Cu or Ag stearates, as boundary lubricants is set forth by F. P. Bowden and D. Tabor in *The Friction and Lubrication of Solids*, at pp 176–227 (Oxford Univ. Press, London, 1950)). The classic boundary lubricants have a polar head such as carboxyl (COOH) that is characterized by high electron density and high chemical activity and that readily aligns itself on other polar sites. Considering iron wear surfaces for purposes of illustration, the polar head anchors itself to the Fe—FeO thereon. A long chain hydrophobic tail portion, R, of the boundary lubricant takes up shear stress between opposing wear surfaces, lowering the coefficient of friction and decreasing wear. However, the classic boundary lubricants typically are fusible. Many classic lubricants have melting points in the range of 80°–250°C and, when melted, do not have sufficiently strong intermolecular forces of attraction, so that the lubricants tend to migrate and the boundary load limit is markedly reduced.

Accordingly, it may be appreciated that there exists a need for a durable boundary lubricant that imparts a low coefficient of friction and superior wear characteristics to metal and ceramic wear surfaces, is non-melting, and is non-migrating.

Critical considerations for wear surfaces in applications such as gas-lubricated hydrodynamic bearings include the low hydrodynamic lift and the low viscosity provided by the hydrodynamic lubrication. At low angular speeds (for example, during starting and stopping), hydrodynamic lift is frequently inadequate to separate the rotating bearing members from the stationary members. The low viscosity of the gaseous working fluids requires that bearings have very small clearances in order to provide useful load capacity and stiffness. For example, a typical sleeve and journal cylindrical bearing of ¼ inch diameter may be limited to an operating radial gap of no more than $40 \times 10^{-6}$ inches.

To provide good dimensional control and to withstand the moving contact that occurs during starting and stopping, the bearing surfaces are usually formed from very hard, wear resistant materials, such as those listed previously, and in particular: nitride steel, hard chromium or nickel plate, glass ceramics sintered alumina, beryllia, or synthetic sapphire. Design limitations and the high cost of fabricating forms for sintered preforms of the hard, refractory ceramic materials have resulted in the use of sprayed coatings of ceramics or cermet alloys. One of the best of these coatings is formed from chromium oxide. The coating is typically applied by hot-powder processes: the oxide of trivalent chromium is applied as a powder using a plasma arc torch or detonation gun, or it may be sputtered using RF energy in a low pressure inert gas. The resulting chromium oxide coating has great hardness, some resiliency and relatively high thermal conductivity.

Chrome oxide and most refractory ceramic coatings that are applied by hot powder processes are porous. Plasma-sprayed chrome oxide, for example, typically contains one to three percent void space or cavities. These cavities are useful as lubricant reservoirs and as storage for wear debris. However, the void volume at the contact surfaces increases the bearing clearance volume, so that the stiffness and bottoming capabilities of the operating bearing are reduced and the rotational velocity at setdown is increased. Also, the voids in ceramics surfaces may be of such dimensions that water and other condensable vapors in the ambient environment are sorbed in the capillaries. As a result, the bearing stiffness may change, even in a sealed environment. An additional detrimental effect of this capillary sorption is that condensed fluids such as water may form corrosion cells between conductive surfaces such as chromium oxide and active metal sublayers. Thus, as an example, etch-roughened beryllium metal was plasma-arc sprayed with a chromium oxide coating of 0.005 inches thickness (nominal) and the coating was exposed to 30 percent relative humidity, then 90 percent relative humidity. As a result, the amount of sorbed surface water increased by approximately 4 milligrams per square inch, and corrosion blisters resulted.

The reliability of devices that incorporate gas-lubricated bearings depends upon their start-stop life. Accordingly, some form of boundary lubricant is utilized in virtually all such devices to reduce friction and wear during starting and stopping. It may thus be appreciated that it is desirable to have an effective boundary lubricant that fills the void spaces and precludes corrosion in the metal substrates of refractory wear coatings.

SUMMARY OF THE INVENTION

A boundary lubricant for metal and ceramic wear surfaces is provided by baking thereon, at about 70°C or above, a layer of a solution of a transition metal complex, including complexes of the higher molecular weight carboxylic acids, such as long chain fatty acids of the type $C_xH_{2x+1}COOH$, wherein $x = 8, 9, 10 \ldots 29$.

A complex of a transition metal (Cr, Mn, Fe, Co, Ni or Al) such as a chromium complex is prepared, e.g., by (1) reducing chromium trioxide using a reducing alcohol such as ethyl or isopropyl alcohol in a low molecular weight aliphatic organic acid such as acetic acid to obtain chromium acetate; and by (2) hydrating and olating the chromium acetate. A solution containing a maximum of about 11 weight percent of the metal complex in trichloroethylene, benzene, isopropanol or similar solvent is then applied as a thin layer on a metal or ceramic wear surface. Exemplary metal complex concentrations for non-porous and porous wear surfaces are about 0.1 weight percent of chromium stearate complex and about 1–2 weight percent of chromium behenate complex, respectively. The layer formed from the metal complex solution is then heated at a temperature within the approximate range 70°–160°C, typically about 100°C, for 1–4 hours to polymerize the metal complex molecules. For porous wear surfaces, fatty acids may be utilized in amounts up to approximately 2 mols of fatty acid per gram atom of chromium, with an optimum fatty acid/chromium ratio being about 1.0 to 1.2 mols fatty acid/gram atom of chromium.

The boundary lubricant anchors to the wear surface and is then cross-linked or polymerized by the heat treatment, forming a solvent-resistant, hydrophobic, durable lubricant that substantially decreases the coefficient of friction, improves the wear characteristics between wear surfaces and contacting surfaces and, in the case of porous ceramic wear surfaces, fills the pores thereof and retards corrosion.

DETAILED DESCRIPTION

Figure 1:
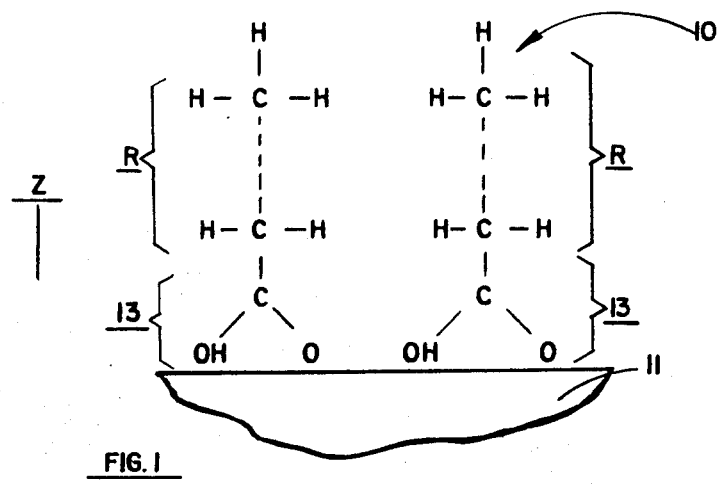
FIG. 1 is a simplified schematic representation of the molecules of a classic boundary lubricant that are adhered to a metallic wear surface.

Referring to FIG. 1, there is shown a greatly simplified representation of a molecular structure 10 of a classic boundary lubricant that is adhered to a wear surface 11, typically a metal or a ceramic. Wear surfaces usually consist of materials such as iron, steel, chromium, nickel, silicon (and the alloys and carbides thereof), quartz, boron carbide, and metal oxides such as chromium oxide and aluminum oxide. For purposes of discussion, the wear surface 11 will be deemed to be formed from iron and to be at least partially oxidized. The prior art lubricant typically is a fatty acid that has a long chain, nonpolar, inert hydrophobic tail R and a polar head 13. The polar head 13 readily aligns itself on polar surface cites such as the Fe—FeO wear surface 11, adhering to the surface by forming valence bonds therewith, and is thus anchored to the surface in a direction, arbitrarily designated the Z direction in FIG. 1, at an angle thereto. The long chain R takes up shear stresses imposed on the wear surface 11, lowering the coefficient of friction and reducing wear.

As discussed previously, classic boundary lubricants such as stearic acid or simple metal stearates have low melting points and insufficiently strong intermolecular forces of attraction, with the result that they tend to migrate from the surface or melt at the elevated temperatures to that wear surfaces frequently attain. In addition, the low melting points of the classic lubricants result in the development of hot spots, that is, isolated areas of high temperature, during the operation of apparatus employing wear surfaces.

Figure 2:
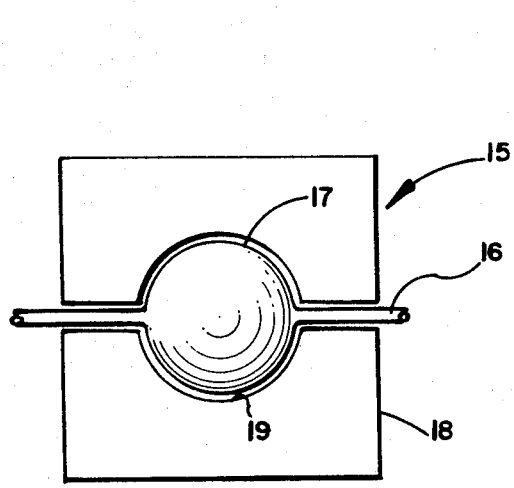
FIG. 2 is a cross-sectional representation of a precision bearing assembly having wear surfaces that require the application of a boundary lubricant.

Referring now to FIG. 2, there is shown a precision bearing assembly 15 that illustrates an additional problem associated with the use of classic boundary lubricants. The assembly 15, which may be used in apparatus such as gyroscopes, has Ni—Cr wear surfaces: a ball shaft assembly 16 has a chrome-plated wear surface 17 on the ball portion thereof; and a rotor 18 has a nickel plated wear surface 19. Although a gaseous cushion, such as hydrogen or air, may be used to prevent contact between the wear surfaces 17 and 19, contact occurs anyway during starts and stops, and a boundary lubricant must be applied to the wear surfaces.

Wear surfaces such as those in the bearing assembly 15 typically have clearances of about 50–300 microinches. Dissimilar metals such as the aforementioned chromium and nickel are used for the wear surfaces so the bearing does not freeze during operation. However, the use of dissimilar metals subject boundary lubricants to an additional limitation. That is, although metals such as chromium and nickel are harder than iron, they are not as polar (active) as iron, and thus provide a weaker anchor for the molecular structure of the lubricant. Consequently, the tendency of the lubricant to migrate and melt and to allow the formation of hot spots is even greater than normal.

The shortcomings of the prior art are overcome by forming a boundary lubricant from compositions selected from metal coordination complexes (also known in the art as "Werner Complexes") of an homologous series of long chain fatty acids. In particular, the compositions are selected from the fatty acid soaps of the hydrated complexes of certain of the transition elements. The fatty acid series consists of carboxylic acids of the type $C_xH_{2x+1}$ COOH, wherein $x = 8, 9, 10, \ldots 29$. The soap-forming transition element is a metal such as Cr, Mn, Fe, Co, Ni or Al that can form coordination complexes. Exemplary fatty acid complexes are the chromium complexes of stearic and behenic acid, i.e., chromium stearate and chromium behenate.

Figure 3A:
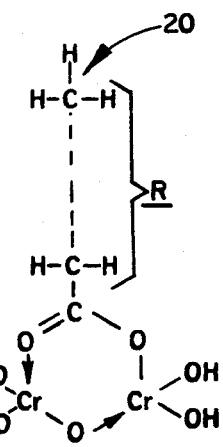
FIG. 3A is a simplified schematic representation of the molecular structure of a metallic complex that may be used to form a boundary lubricant of the present invention.

Referring now to FIG. 3A, there is shown a schematic representation of the conceptual molecular structure of one form of a chromium complex such as chromium stearate, designated generally by the reference numeral 20, that may be used to form a boundary lubricant of the type of the present invention. Chromium stearate possesses the ability to form strong valence bonds to the surfaces of many metals and ceramic materials, thus anchoring itself securely along an axis arbitrarily designated the Z-axis. Additionally, chromium stearate cross links or polymerizes along an arbitrarily designated X-Y plane that is generally parallel to the plane of the wear surface. As a result, the molecules are anchored in X, Y, and Z directions.

Figure 3B:
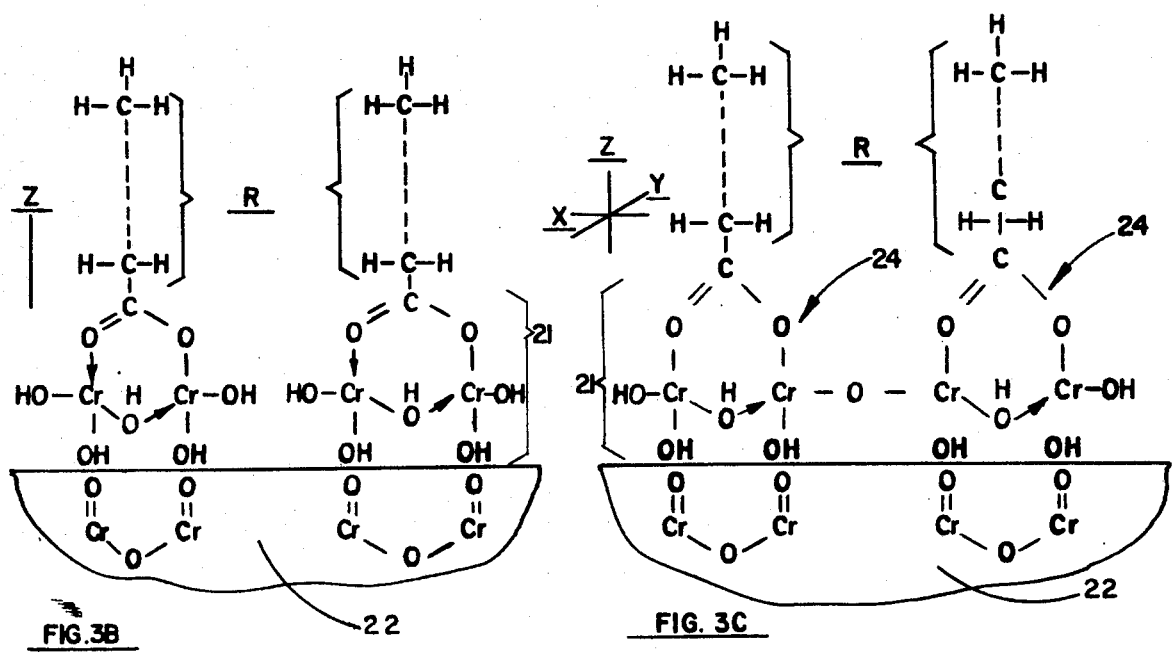
FIG. 3B is a simplified schematic representation of the mode of adhesion to a wear surface of one embodiment of a boundary lubricant of the present invention.
Figure 3C:
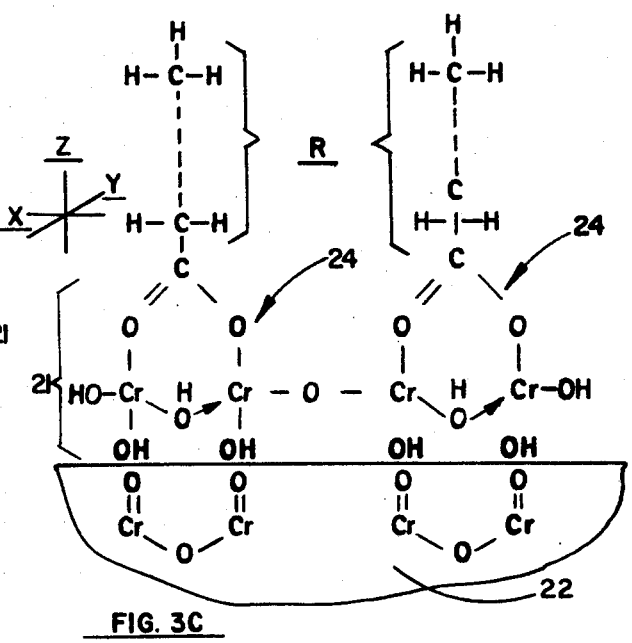
FIG. 3C is a simplified schematic representation of the adhesion to a wear surface of, and cross linking between, the molecules of one embodiment of a boundary lubricant of the present invention.

More specifically, referring now to FIG. 3C, the chromium complexes possess (1) a highly polar head portion 21 that chemically adheres in the Z direction to a metal or ceramic wear surface 22 and (2) a long chain portion R that takes up shear stresses, resulting in a low coefficient of friction and decreased wear, and that may be crosslinked or polymerized in an X-Y direction to impart durability to the lubricant.

Various methods of preparation of the complexes of inorganic and organic salts and soaps of the transition elements are treated in the literature. Accordingly, extensive explanation is given here primarily regarding the novel features of the present invention.

Briefly, the transition element complexes used here were prepared by (1) reducing chromium trioxide by a reducing alcohol such as ethyl or isopropyl alcohol and in a low molecular weight aliphatic organic acid (which is non-reducing and sufficiently polar to be extracted into a water layer) such as acetic acid to obtain trivalent chromium acetate; then (2) hydrating and olating the resulting trivalent chromium acetate. The complexes have also been prepared by heating a mixture of the appropriate fatty acid, a reducing alcohol, acetic acid, chromium trioxide and water in appropriate amounts to a preferred temperature within the approximate range of 60° to 70°C.

For lubrication purposes, it is desirable to have a chloride-free compound. Most references cite the possibility of reducing hexavalent chromic oxide as an in situ source of complexable chromium, but cite only chromyl chloride or trivalent salts and do not give examples of good $CrO_3$ reaction conditions. Furthermore, the heat of reduction of $CrO_3$ is high and can cause runaway reaction. In the absence of an acid reserve, such reduction is not complete, and unidentified insoluable masses result. The method of the present invention, including the utilization of a liquid phase (a ternary azeotrope of water-benzene-isopropanol); boiling in the preferred temperature range 60°-70°C to prevent overheating and to maintain olation conditions; and the use of an auxilary organic acid of low molecular weight (e.g. acetic acid), is not disclosed in prior art.

In an exemplary laboratory-scale method of preparing the boundary lubricant of the present invention, e.g., chromium behenate complex soap, chromic anhydride ($CrO_3$), purified water, and glacial acetic acid are combined in the approximate weights 1 gm, 2 gm and 2.4 gm, respectively. Subsequently, 4 gm of behenic acid, followed by 120 ml benzene (which sets up an upper organic layer), a maximum of 5 ml water, and 70 ml isopropyl alcohol are added to the solution. This solution is then refluxed (at about 65°C) and stirred for a minimum of about 3 days to complete reduction and approximately 90% of olation.

Next, $Na_2CO_3$ is heated at 125°-500°C until thoroughly dried (for example drying takes about one hour at 175°C), is dissolved to a concentration of 5 gm-mole per liter of purified water, and this solution is then added to the behenate solution to adjust the pH of that solution to about 7.3 to 8.1. Initially, about 7.5 ml are required; then after 16 hours, 0.3 to 0.4 ml are added; and, in another 20 hr., olation is considered complete.

The pH-adjusted behenate solution is then washed to remove any emulsion-forming impurities. The washing is accomplished by adding about 200 ml of deionized water to the behenate solution in the organic layer, agitating the solution for several hours while maintaining the temperature of the solution at about 70°C to break up any emulsion, then decanting any resulting organic layer (top layer) of benzene solution and parting the aqueous layer using a separatory funnel. Several washings may be required to remove all sodium acetate, alcohol and other water-soluble impurities.

Finally, residual water and alcohol are removed by azeotropic distillation at reduced pressure. Complex chromium behenate remains in benzene solution. This resulting complex has a nomimal fatty acid mol/-chromium gm-atom ratio of 1.175 after evaporation, an initial melting point of 60°-80°C, and may be polymerized to a solid that decomposes at about 360°C.

The above-described method of preparation is illustrative only. The steps set forth therein may be accomplished in other ways. Also, the overall process used to form the behenate complex solution may differ. For example, chromyl chloride may be reduced by alcohol to chromic chloride, and the chromic chloride reacted with carboxylic acid to form a chromium complex. This indirect method of forming the chromium complex using an intermediate chloride compound is taught in an article by F. B. Hauserman entitled "*Chromium Complexes*", in Metal-Organic Compounds, pp 338–56, Advances in Chemistry Series, Vol 23, Am. Chem. Soc. (1969).

The transition element complex such as chrome benenate complex soap may be applied to wear surfaces as a 0.1 to 11 weight percent solution of trichloroethylene, benzene, isopropanol, or other solvents to form a thin layer thereon. The layer is then subjected to a heat treatment, i.e., a bake or a vacuum bake, to effect polymerization. The polymerized chromium complex is then ready for use as a boundary lubricant as contemplated by the present invention.

The mechanism for Z-direction anchoring and X-Y plane polymerization for an exemplary chromium behenate or stearate boundary lubricant is represented in FIG. 3. As mentioned previously, the schematic molecular structure 20 of chromium stearate is shown in FIG. 3A. Upon application of the chromium complex-containing solution to a metal wear surface 22 (FIG. 3B) having oxide formed thereon, the multi-valence states of chromium (+3, +5, +6) are believed to form covalent, coordinate, and other strong valence bonds with the metal or ceramic wear surface. Next, and referring to FIG. 3C, the lubricant is heated to effect cross linking in the X-Y plane. Initially, the chromium complexes in the boundary lubricant align in parallel relationship on the wear surface 22 (see also FIG. 3B) due to the polar forces of attraction therebetween. Then, the compounds cross link at bases 24 of the molecules by condensation polymerization between vicinal hydroxyl, chloro, or alkoxy groups.

Typically, heating is done at about 100° to 160°C for 1-4 hours at atmospheric pressure or at a vacuum of approximately 10–200 $\mu$ of mercury. The temperature is chosen so as to be below the temperature (e.g. 360°C) for which substantial pyrolitic decomposition occurs. The resulting baked lubricant films are extremely tenacious, solvent resistant and hydrophobic, and are therefore of greater durability than the prior art boundary lubricants. In addition, coefficients of friction between wear surfaces are reduced, providing better wear characteristics and preventing galling and other undesirable effects.

Chromium stearate, oil base lubricants (which are not true boundary lubricants), and classic boundary lubricants (lithium stearate, mellissic acid, phthalocyanine, and sodium lauryl sulfate) were vacuum baked on contiguous chrome versus nickel wear surfaces 17 and 19 of a bearing assembly similar to the assembly 15 shown in FIG. 2. The baking was for about 3 to 4 hours at 90°C using a subatmospheric pressure of 10–200 $\mu$ of mercury. Coefficients of friction were then measured before rotation and after various periods of rotation of bearing wear surfaces that used the different types of lubricants.

The coefficients of friction of wear surfaces that were lubricated with chromium stearate were low. For a typical bearing, the above-described vacuum bake increased the melting point of the chromium stearate boundary lubricant from 65°C to about 110°C and provided friction coefficients of 0.10 – 0.20 initially, 0.20 – 0.30 after 500–3000 revolutions, and 0.30 – 0.40 after 5000 revolutions. There was no debris formation on the wear surfaces.

The oil base lubricants used were polyisobutylenes in light mineral oil, and compounds No. 3K93-1 to -3, obtained from the Bray Oil Company, Los Angeles, California.

For usage of as much as 500 revolutions, the friction coefficients provided by the oil-base lubricants for rough-surfaced bearings (1–2 microinches rms roughness) were comparable to the previously-described coefficients provided by the chromium stearate. In all other instances, the oil base lubricants were inferior to the chromium stearate. That is, for more than 500 revolutions of the rough-surfaced bearings, and for even fewer than 500 revolutions of smoother-surfaced bearings (about 0.5 microinches rms roughness), the coefficients of friction greatly exceeded those provided by chromium stearate. For example, using the smoother bearings, Bray Oil Co. compounds No. 3K93-1, -2, and -3 gave initial friction coefficients of 0.29, 0.43, and 0.21, respectively, and after 500 revolutions, gave friction coefficients of 0.80, 1.00 and 0.61. Debris buildup was at times very pronounced for the oil base lubricants.

For the classic boundary lubricants, the coefficients of friction were within the range 0.16 for mellissic acid to 0.27 for behenic acid amide of diethanolamine initially, and within the range 0.60 for mellissic acid to 0.80 for phthalocyanine after 500 revolutions. As is evident, the classic boundary lubricants (and oil-base lubricants) produce coefficients after only 500 revolutions that are considerably higher than the coefficients provided by the chromium stearate after 5000 revolutions. In addition, the classic boundary lubricants evidenced debris buildup ranging from light to heavy.

In accordance with the present invention, the fatty acid hydrated complexes of certain transition elements may also be used as porosity-filling boundary lubricants. The fatty complexes of transition elements such as chromium and iron have several characteristics in common — they are soluble in non-polar solvents such as aromatic or chlorinated aliphatic solvents, are polymerized at conveniently low temperatures (typically 60° to 100°C) to rubbery solids that melt at much higher temperatures (typically 160° to 220°C or even higher temperatures) — such that boundary lubricants may be readily formed therefrom.

The fatty complexes of the transition elements are prepared in solution as described previously. Again using chromium behenate as an example, the fatty soap may be used as a porosity-filling boundary lubricant for wear surfaces such as those of the bearing assembly 15 (FIG. 2) where the wear surfaces comprise material such as porous ceramic. The chromium complexes with fatty acids, such as chromium behenate complexes, have very high solubility in non-polar solvents such as benzene. While there appears to be no limit to the solubility of chromium behenate complexes, a solution of bluish 1.9 mol behenic acid/gram atom of Cr, which was prepared as an 11 weight percent concentration in benzene, remained stable in excess of 6 months at 25°c.

To deposit the exceedingly thin films of lubricant that are appropriate for non-porous (e.g., sapphire) bearings, low concentrations of the order of 0.1 weight percent or less of the complexes may be used. For the porous plasma-sprayed coatings, however, much higher concentrations are convenient. For example, chromium behenate may be applied to parts having porous wear surfaces by immersing the parts in a 1–2 weight percent solution of the chromium behenate in benzene, optionally using ultrasonic agitation for 1–5 minutes, then drying the parts and wiping to remove any excess lubricant. The minimum practical complex concentration for porous wear surfaces is 1 weight percent, since lower concentrations may require an excessive number of immersions. This method is illustrative only, for other methods may be used.

The initial coating may be dried of solvent at a temperature above the (unpolymerized) melting point and below that at which speedy polymerization occurs (typically occurs at and above 65° to 85°C). Additional coats may then be applied as required until the porosity is filled. The still-molten excess is removed by thorough rubbing with an absorbent material and then polymerization is completed at or above the range 65° to 85°C.

In order to determine the effect of the present boundary lubricant on the coefficient of friction of porous wear surfaces, chrome-oxide coated spin bearings were prepared for operation in various ways, including application of the present boundary lubricant. The average start voltage, which is roughly proportional to the coefficient of friction, was then determined both before and after 60 start-stop cycles. Bearings that were cleaned using glow discharge required average initial and final start voltages of 152 and 171 volts, respectively. Bearings that were cleaned in detergent and organic solvents such as trichloroethylene required average initial and final start voltages of 132 and 148 volts, respectively. Finally, bearings to which chrome behenate boundary lubricant had been applied required average initial and final start voltages of 125 and 122 volts, respectively. The results for the chrome behenate lubricated bearings indicate the starting torque is lowered using the boundary lubricant of the present invention and, unexpectedly, decreases slightly with use.

The benefit of fatty chromium (III) complexes is also obtained to a large extent when they are not fully polymerized. Thus, good results are obtained in sliding wear tests on surfaces coated with incompletely polymerized chromium behenate. The friction between nickel and chromium was low and constant after long periods of rubbing contact. Also, a slight but persistent additional reduction in bearing start voltages occurred after chromium oxide-coated bearings were coated with diluted chromium behenate complex that was baked at a relatively low temperature, i.e., not over 100°C.

Humid-environment corrosion tests were also performed. Beryllium metal gas bearing elements were anodized in a conventional dichromate-chromic acid solution, plasma-arc sprayed with chromium oxide, and impregnated with chromium behenate, which was then polymerized. A number of parts were tested by exposure to saturated water vapor in a sealed chamber at 60° to 85°C for 16 to 54 hours. The parts exhibited no evidence of blistering or corrosion after the test. This is indicative that the behenic acid complex provides permanent filling of the porosity in the chrome-oxide coating, in addition to being an excellent boundary lubricant, as described in the preceding paragraph.

The amount of boundary lubricant that is applied to porous wear coatings and the method of application and removal of any excess have relatively little effect upon the continuing excellent performance of the present boundary lubricants. In addition, the amount of fatty acid or organic polyacid that can be incorporated into the preparation of the complex chromium soap is not fixed, and can vary depending upon the degree of coupling and the complex and ancillary substitute groups. However, there is an optimum range from the fatty acid/chromium ratios. That is, the maximum useful ratio of fatty acid to chromium appears to be about 2:1. For example, when porous bearings similar in configuration to the bearing assembly 15 were impregnated with the previously mentioned chromium complex that contained 1.9 mols of behenic acid per gram atom of chromium, and then polymerized, the bearings exhibited traces of debris after about 50 start-stop cycles. This debris was rich in free behenic acid. However, it was determined that a ratio of 1.0 to 1.2 mols of behenic acid per gram atom of chromium gave excellent lubrication and no debris was apparent after more than 8000 start-stop cycles.

The minimum useful fatty acid/chromium ratio for porous wear surfaces is primarily dependent upon the extent of lubricating effect that is desired. Using 0.5 mol of stearic acid per gm-atom of chromium, a decided lubricating effect is observed during sliding wear tests. Still better lubrication is observed using a more fatty acid.

It should be noted that when the hydrogen atoms of the fatty acid are replaced by, e.g., flourine, the compound becomes less stable. Thus, when chromium (III) acetate was olated with perflourotanoic acid, the complex equilibrated readily but was largely decomposed by a 90°C vacuum bake, and was short-lived as a lubricant. Similarly, a benzoate complex lost much weight during polymerization and was inferior to the aliphatic acid complex compounds.

Semi-polar waxy substrates such as the diethanolamide of behenic acid [$(C_{21}H_{43}CON(C_2H_4OH)_2$] have moderately high melting points (105°C for diethanolamide of behenic acid containing traces of congener diethanolamine esters) and have excellent lubricating characteristics on ceramic oxides. Unfortunately, when substances of this class are used as boundary lubricants, their effectiveness is very sensitive to the amount applied, since a slight excess in the pores is extended upon rubbing contact. However, this class of substances provides coatings that are more easily removed than coatings formed from the boundary lubricants of the present invention, yet resist the solvents used for shop cleaning. In addition, substances from this class may be used to prevent corrosion of porous wear surfaces. Accordingly, such substances may be used as coatings for wear surfaces during fabrication and/or storage, then removed (together with the debris and abrasives picked up during machining) and replaced by the permanent boundary lubricant of the present invention, prior to the utilization of the device that incorporates the wear surfaces.

Though the enumerated examples treat only chromium stearate and behenate, in general R (refer to FIGS. 3A, B, C) may be selected from a wide variety of long chain moieties. R may be, but is not restricted to, a long chain fatty acid within the range $C_8$ to $C_{29}$. In addition, R may be saturated, as stearate, $H_3C-(CH_2)_{16}-$ ;

unsaturated, as oleate, $H_3C(CH_2)_7-CH=CH-(CH_2)_7-$ ;

or branched, as 2-ethyl hexoate

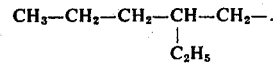

Thus, there has been described a composition and method for forming an improved boundary lubricant comprising polymerizable metal complexes of certain transition elements with, e.g., long chain fatty acids, an example of which is chromium behenate. The boundary lubricant formed from the composition provides excellent lubrication and wear-decreasing characteristics, and also excellent porosity-filling qualities such that it may be used in conjunction with porous wear surfaces. Preferred compositions, temperatures, and other parameters for preparation and application of the lubricant have been described. The scope of this invention is limited, however, only by the claims appended hereto and equivalents thereof.

Having thus described a preferred embodiment of the invention, what is claimed is:

1. A method of boundary lubricating a wear surface, said method compirising:
    forming a chlorine-free metallic coordination complex of a long chain fatty acid, wherein said fatty acid is selected from an homologous carboxylic series and wherein the metallic constituent is a transition metal capable of forming coordination complexes selected from Cr, Mn, Fe, Co, Ni, and Al, by;
    reducing an oxide of said transition metal to an acetate of said transition metal,
    hydrating said acetate of said transition metal, olating the product of said hydrating step,
    forming a coating of said chlorine-free metallic coordination complex on said wear surface; and
    heating the coated wear surface to polymerize said metallic coordination complex and to anchor said complex to said wear surface.

2. The method of boundary lubricating a wear surface recited in claim 1 wherein said long chain, fatty acid is saturated and is selected from HCOOH, R = $C_xH_{2x+1}$, where X is greater than or equal to 8 and less than or equal to 29.

3. A method of boundary lubricating a wear surface said method comprising:
    forming a chlorine-free metallic coordination complex of a long chain fatty acid, wherein said fatty acid is selected from an homologous carboxylic series and wherein the metallic constituent is the transition metal Cr capable of forming coordination complexes, said chlorine-free metallic coordination complex being formed by:
    reducing chromium trioxide to chromium acetate, hydrating said chromium acetate, and
    olating the product of said hydrating-step;
    forming a coating of said chlorine-free metallic coordination complex on said wear surface; and heating the coated wear surface to polymerize said metallic coordination complex and to anchor said complex to said wear surface.

4. The method of boundary lubricating a wear surface recited in claim 2 wherein:
said long chain fatty acid is $C_{17}H_{35}COOH$; and
said heating step comprises heating said coated wear surface to approximately 70–160°C for about 1–4 hours.

5. The method of boundary lubricating a wear surface recited in claim 1 wherein:
said wear surface comprises porous ceramic material;
said fatty acid is $C_{21}H_{43}COOH$;
said metallic constituent is Cr;
said metallic coordination complex contains a ratio of moles of $C_{21}H_{43}COOH$ to gram atoms of chromium that is within the approximate range (0.5–2.0)/1; and
said heating step is done at a temperature of at least about 70°C.

6. The method of boundary lubricating a wear surface recited in claim 2 wherein said ratio is approximately 1/1.

7. The method of boundary lubricating a wear surface recited in claim 1 wherein said step of forming a coating comprises:
dissolving said chlorine-free metallic coordination complex in a substantially water-free organic solvent; and
coating said wear surface with said solvent containing said chlorine-free metallic coordination complex.

8. The method of boundary lubricating a wear surface recited in claim 7 wherein said dissolving step comprises dissolving a sufficient quantity of said metallic coordination complex in said solvent to form a solution consisting of 0.1 to 11 weight percent of said metallic coordination complex; and
said solvent is selected from trichloroethylene, benzene and isopropanol.

9. In combination, a method of protecting a porous wear surface from corrosion and of boundary lubricating said wear surface, said method comprising the steps of:
forming a first diethanol amide of behenic acid coating on said wear surface;
removing said first coating;
said boundary lubricating the wear surface by a method comprising:
forming a chlorine-free metallic coordination complex of a long chain fatty acid, wherein said fatty acid is selected from an homologous carboxylic series and wherein the metallic constituent is a transition metal capable of forming coordination complexes selected from Cr, Mn, Fe, Co, Ni, and Al by:
reducing an oxide of said transition metal to an acetate of said transition metal,
hydrating said acetate of said transition metal,
olating the product of said hydrating step;
forming a coating of said chlorine-free metallic coordination complex on said wear surface; and
heating the coated wear surface to polymerize said metallic coordination complex and to anchor said complex to said wear surface.

* * * * *